United States Patent [19]

Okada et al.

[11] 4,201,198
[45] May 6, 1980

[54] ENDOSCOPE HAVING A SEPARABLE CONNECTION TO A PHOTOGRAPHING DEVICE

[75] Inventors: Takeshi Okada, Hachioji; Mototugu Ogawa, Chofu, both of Japan

[73] Assignee: Olympus Optical Co., Ltd., Tokyo, Japan

[21] Appl. No.: 861,284

[22] Filed: Dec. 16, 1977

[30] Foreign Application Priority Data

Dec. 27, 1976 [JP] Japan .................. 51-176551[U]

[51] Int. Cl.$^2$ .............................................. A61B 1/04
[52] U.S. Cl. ........................................ 128/4; 128/6; 254/134.3 R
[58] Field of Search ................................ 128/4–8; 354/62, 63; 223/99; 254/134.3 R, 134 FT

[56] References Cited

U.S. PATENT DOCUMENTS

| | | | |
|---|---|---|---|
| 424,518 | 4/1890 | Van Norman | 223/99 |
| 2,612,546 | 9/1952 | Romsos | 254/134.3 FT |
| 2,641,977 | 6/1953 | Vji et al. | 128/8 X |
| 3,041,043 | 6/1962 | Harden | 254/134.3 FT |
| 3,224,732 | 12/1965 | Williams | 254/134.3 FT |
| 3,253,524 | 5/1966 | Ashizawa et al. | 128/6 UX |
| 3,330,533 | 7/1967 | Blume | 254/134.3 FT |
| 3,866,602 | 2/1975 | Furihata | 128/6 |
| 4,038,977 | 8/1977 | Okada | 128/6 |
| 4,085,742 | 4/1978 | Okada | 128/4 |
| 4,102,478 | 7/1978 | Samoilov | 223/99 |

FOREIGN PATENT DOCUMENTS

| | | | |
|---|---|---|---|
| 521988 | 2/1956 | Canada | 223/99 |
| 344145 | 3/1931 | United Kingdom | 223/99 |

*Primary Examiner*—Edgar S. Burr
*Assistant Examiner*—Steven A. Bratlie

[57] ABSTRACT

An endoscope provided with a photographing device includes a film feeding wire and a latch. The film feeding wire has its one end secured to the outer end of a film loaded in the photographing device which is disposed in the distal end of the endoscope. The other end of the film feeding wire is provided with a stop which has a larger diameter than the wire. The latch made of elastic material comprises a loop section and a latch section. The loop section is secured to the forward end of an operation wire extending through a sheath and usually has an opening larger than the stop of the film feeding wire. The latch section is connected to the loop section and adapted to hold the film feeding wire. When the film feeding wire is pulled into the latch section from the loop section outside the distal end portion of the endoscope, the film feeding wire is connected to the operation wire. For disconnection from the operation wire, the film feeding wire is pulled back into the loop section from the latch section.

5 Claims, 15 Drawing Figures

ENDOSCOPE HAVING A SEPARABLE CONNECTION TO A PHOTOGRAPHING DEVICE

BACKGROUND OF THE INVENTION

This invention relates to an endoscope having a photographing device disposed in its distal end portion, comprising a latch which easily achieves a connection and disconnection between an operation wire and a film loaded in the photographing device.

In using a conventional endoscope provided in its distal end portion with a photographing device such as a gastrocamera, an elongated through hole is formed in the outer end of a film loaded in the photographing device, and a T-shaped latch member is attached to the distal end of an operation wire. The latch member is inserted into the elongated through hole of the film, with its head aligned therewith and then rotated about right angles. Thus, the film is secured to the latch member and the operation wire is connected to the film by the latch member. To achieve such connection between the film and the operation wire, much time is required. Further the latch member should be made extremely small, since it is desired that the distal end portion of an endoscope be as thin as possible. The latch member being small, more time is required in order to connect the film to the operation wire. Moreover, since the connection between a film and the operation wire is achieved in the semi-darkness, the work is difficult for an endoscope operator, particularly a presbyope operator.

SUMMARY OF THE INVENTION

An object of this invention is to provide an endoscope having a photographing device, which is provided with a latch for alternately achieving engagement and disengagement between an operation wire and a film loaded in the photographing device.

Another object of this invention is to provide an endoscope having a photographing device, which is provided with a latch for easily achieving engagement and disengagement alternately between an operation wire and a film loaded in the photographing device, outside the distal end portion of the endoscope.

According to this invention, there is provided an endoscope comprising a sheath, a distal end portion provided at one end of the sheath, a photographing device provided in the distal end portion and having a rolled film loaded therein, a film feeding wire connected to the outer end of the film, a stop formed at the free end of the film feeding wire and having a larger diameter than the film feeding wire, an operation wire extending in the sheath, and a latch comprising a loop secured to the distal end of the operation wire and having an opening larger than the stop and a latch section formed integral with the loop for holding the film feeding wire.

DETAILED DESCRIPTION OF THE PREFERRED EMBODIMENTS

Figure 1:
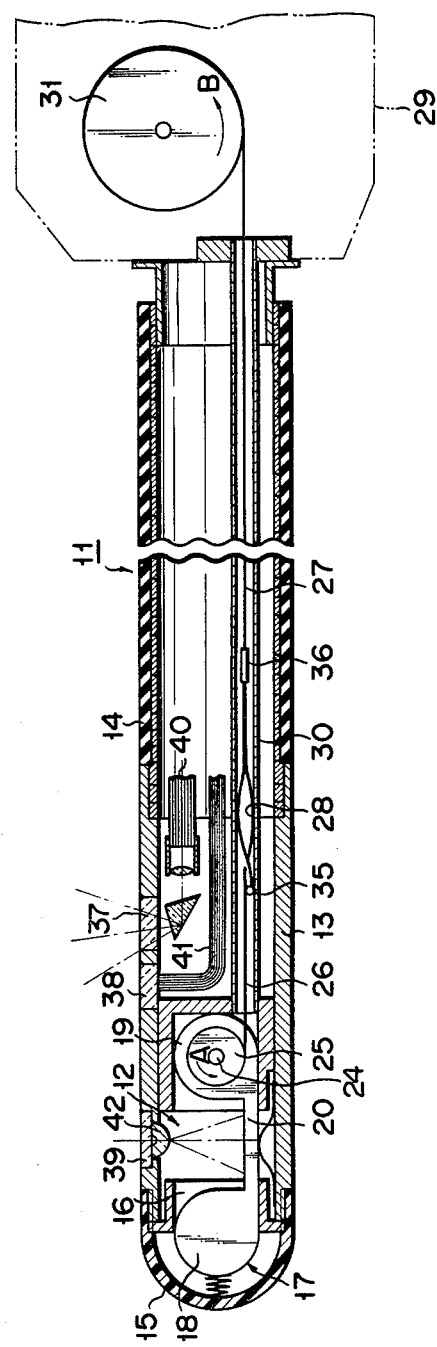
FIG. 1 is a vertical cross-sectional view of an endoscope according to this invention.

Throughout the drawings, the same or similar parts or components are denoted by the same reference numerals.

Figure 2:
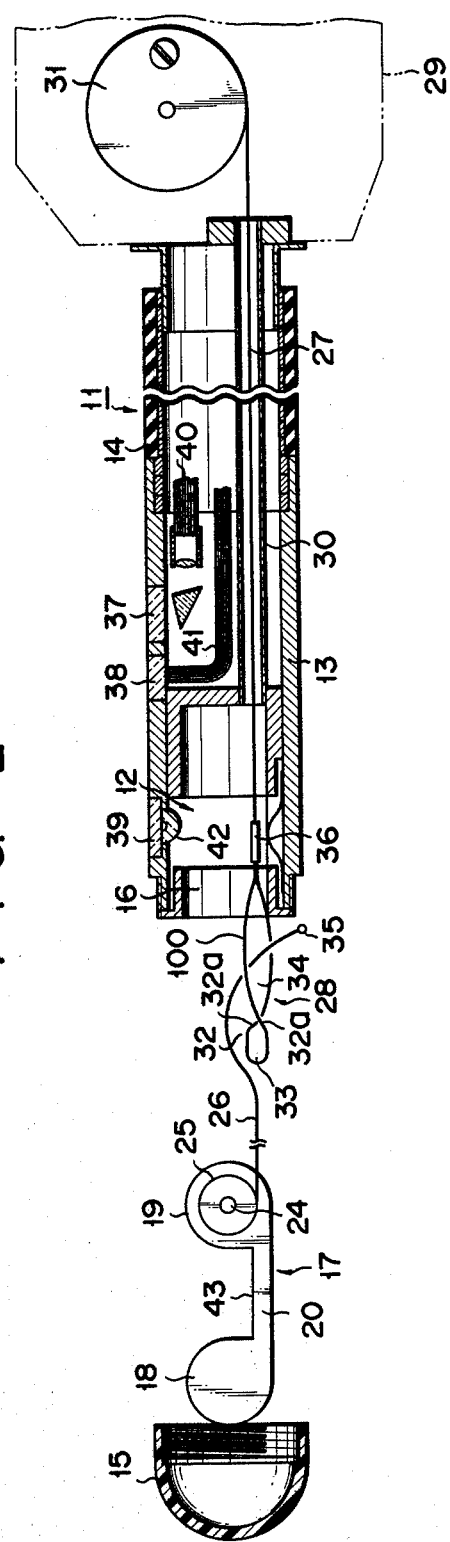
FIG. 2 is another vertical cross-sectional view of the endoscope shown in FIG. 1, with a cap unscrewed and a film cassette taken out.

An endoscope 11 shown in FIG. 1 comprises a distal end portion 13 which is a rigid tube. In the distal end portion 13 there is disposed a photographing device 12, e.g. a gastrocamera. One end of the distal end portion 13 makes a screw engagement with the forward end of a flexible tubular sheath 14. The other end of the distal end portion 13 is also in a screw engagement with a semi-spherical cap 15. Defined in the distal end portion 13 and the cap 15 is a cassette chamber 16 to receive a film cassette 17. Once the cap 15 is removed from the distal end portion 13 as shown in FIG. 2, the film cassette 17 can be taken out from the cassette chamber 16.

Figure 3:
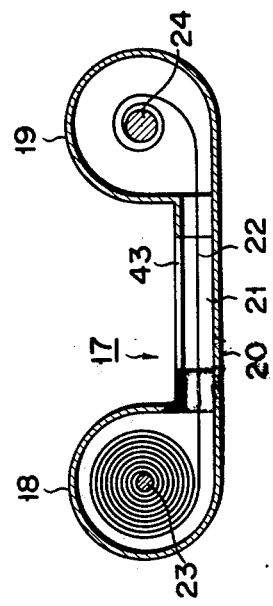
FIG. 3 is a vertical cross-sectional view of the film cassette used in the endoscope shown in FIG. 1.

The film cassette 17 comprises a substantially hollow cylindrical film containing section 18, a substantially hollow cylindrical film take-up section 19 and a connecting section 20 which tangentially connects the film containing section 18 and the film take-up section 19. As illustrated in FIG. 3, a film passage 21 is formed in the connecting section 20. Through the film passage 21, a film 22 is fed from the film containing section 18 to the film take-up section 19. The film 22 is exposed as it passes the central part of the film passage 21, as will be described later. A shaft 23 around which the unexposed film 22 is wound is provided in the center of the film containing section 18. Similarly, a film take-up shaft 24 is disposed in the center of the film take-up section 19. The outer end of the film 22 is secured to the film take-up shaft 24. The film take-up shaft 24 protrudes outside the film take-up section 19, and a film take-up pulley 25 is secured to the protruding end of the shaft 24.

Around the film take-up pulley 25, a film feeding wire 26 is wound, with its one end secured to the pulley 25. As the wire 26 is pulled out, the pulley 25 rotates in the direction of arrow A in FIG. 1 so as to enable the take-up shaft 24 to take up the film 22, thereby to move the film 22 through the film passage 21 toward the film winding section 19.

The other end of the film feeding wire 26 is connected to an operation wire 27 by a latch 28, which will be described later. The operation wire 27 penetrates a guide pipe 30 extending through the sheath 14 and reaches an operation section 29 of the endoscope 11. One end of the operation wire 27 is secured to a wire take-up pulley 31 provided at the operation section 29. As the pulley 31 is rotated in the direction of arrow B in FIG. 1, the operation wire 27 is pulled toward the operation section.

Figure 4:
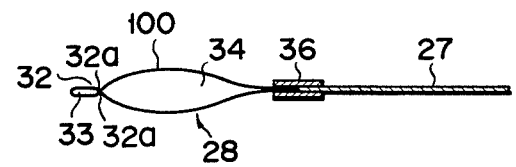
FIGS. 4 and 5 schematically show the latch of the endoscope shown in FIG. 1.

The latch 28 is connected to the other end of the operation wire 27 and serves to detachably connect the film feeding wire 26 to the operation wire 27. As shown in FIGS. 2 and 4, the latch 28 comprises a loop of a thin elastic wire 100. The wire 100 is crossed at portions 32a near its forward end, thereby forming a smaller loop 33 and a larger loop 34 at the both sides of a crossed portion or neck 32. A stop 35 is formed at the forward end of the wire 26 which is thicker than the wire 26. The smaller loop 33, on the one hand, has such an opening that it allows the wire 26 to pass therethrough but does not permit the stop 35 to pass therethrough so as to prevent the wire 26 from being pulled out thereof. The larger loop 34, on the other hand, allows the stop 35 as well as the wire 26 to pass through it.

When the film feeding wire 26 is forcibly inserted into the neck 32, the neck 32 is widened and allows the wire 26 to pass through, but, the portions 32a constituting the neck 32 are so rigid that the neck 32 would not expand to such an extent as to allow the stop 35 to pass through. Thus, if the wire 26 passing through the larger loop 34 is strongly pulled toward the smaller loop 33 from the larger loop 34, it slips into the smaller loop 33 without being pulled off the neck 32. In this way, the film winding wire 26 is easily and unfailingly latched by the latch 28. The latch 28 is attached to the operation wire 27 by a coupling means 36.

The distal end portion 13 has a view window 37 and an illumination window 38 which are positioned rearwardly of the cassette chamber 16 and which are arranged in tandem on the lateral wall of the distal end portion 13. Further, a photographing window 39 is formed in that lateral wall portion of the distal end portion 13 which communicates with the cassette chamber 16.

The view window 37 is optically coupled to the optical unit of the operation section 29 by means of an image guide fiber bundle 40 extending through the sheath 14. Similarly, the illumination window 38 is optically coupled also to the optical unit by means of a light guide fiber bundle 41 extending through the sheath 14. Inside the cassette chamber 16 an optical unit 42 of the photographing device 12 is positioned on the photographing window 39. An image from the photographing window 39 is focussed on the film 21 through an exposure window 43 formed on the central portion of the film cassette 17.

Before the sheath 14 is inserted into a human body cavity, the film cassette 17 is loaded into the cassette chamber 16 of the distal end portion 13 in the following manner. First, the cap 15 is removed from the distal end portion 13, and the cassette chamber 16 is opened. Then, the forward end of the operation wire 27 in the guide pipe 30 is drawn out together with the latch 28 secured to the wire 27. The free end of the film feeding wire 26 with the stop 35 is inserted into the larger loop 34 of the latch 28 and then is strongly pulled against the neck 32 of the latch 28. Thus, the wire 26 slips into the smaller loop 33 while widening the neck 32. Once set in the smaller loop 33, the wire 26 would not slip out of the latch 28 since the stop 35 is provided. As a result, the film feeding wire 26 is connected to the operation wire 27 by means of the latch 28. After the film cassette 17 is set in the cassette chamber 16, the operation wire 27 is pulled into the guide pipe 30. Finally, the cap 15 is attached to the distal end portion 13 as shown in FIG. 1.

Figure 5:

When the operation wire 27 is pulled fully toward the operation section 29 by means of the pulley 31, the latch 28 made of an elastic wire is also drawn toward the operation section 29. As the latch 28 is drawn in this way, both the smaller loop 33 and the larger loop 34 are made flat as shown in FIG. 5. This makes it more difficult for the film feeding wire 26 to slip out of the smaller loop 33.

The operation wire 27 is further pulled toward the operation section 29, as the wire take-up pulley 31 is rotated further in the direction of arrow B. Thus the film feeding wire 26, which is connected to the operation wire 27 by means of the latch 28, is drawn further toward the operation section 29, thereby rotating the film take-up pulley 25 as well as the film take-up shaft 24. The pulleys 25 and 31 have such diameters that the pulley 25 rotates to wind the film 22 for the one-frame distance every time the pulley 31 is rotated through 360°, for example.

After a necessary number of pictures are taken by the photographing device 12, the cap 15 is detached from the distal end portion 13, and then the film cassette 17 is taken out together with the film feeding wire 26 and the latch 28. Then, the film feeding wire 26 in the smaller loop 33 is strongly pulled to the larger loop 34 of the latch 28 and thus slips into the larger loop 34 with the neck 32 widened. As a result, the wire 26 can be easily detached from the latch 28.

Figure 6:
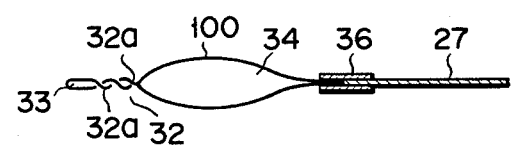
FIGS. 6 and 7 schematically show another embodiment of the latch.
Figure 7:
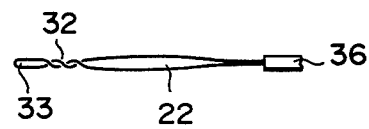

FIGS. 6 and 7 show another embodiment of a latch. This latch 28 differs from the latch 28 shown in FIGS. 4 and 5 in that it is made of an elastic wire 100 which is twisted at least once at wire portions 32a to form a neck 32, a smaller loop 33 and a larger loop 34. The film feeding wire 26 is inserted into the larger loop 34 and then strongly pulled toward the neck 32. Thus, the wire 26 slips into the smaller loop 33 with the neck 32 widened. Once set in the smaller loop 33, the wire 26 would not slip into the larger loop 34 during the photographing operation.

Figure 8:
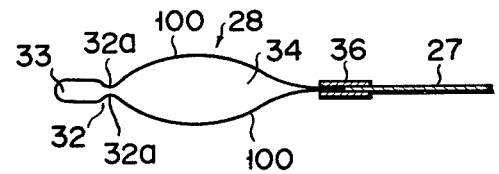
FIGS. 8 and 9 schematically show still another embodiment of the latch.
Figure 9:
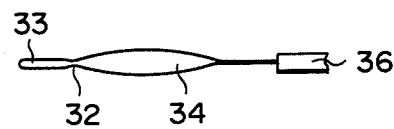

FIGS. 8 and 9 show another embodiment of a latch. This latch 28 is such that the forward portions 32a of a loop of an elastic wire 100 define a gap which is narrower than the diameter of the film feeding wire 26. The gap is such that, when the wire 26 is strongly pulled, it can pass through the gap but the stop 35 cannot pass therethrough.

Figure 10:
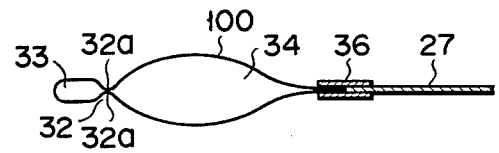
FIGS. 10 and 11 schematically show a further embodiment of the latch.
Figure 11:
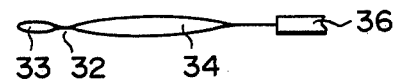

FIGS. 10 and 11 show still another embodiment of a latch. This latch 28 is made of an elastic wire 100, the portions 32a of which are in mutual contact and form a neck 32. Unlike in the latch 28 shown in FIGS. 8 and 9, there is no gap between the portions 32a. Thus, it is a little more difficult for the film feeding wire 26 to pass through the neck 32. But once set in the smaller loop 33, the wire 26 becomes less likely to slip back into the larger loop 34.

Figure 12:
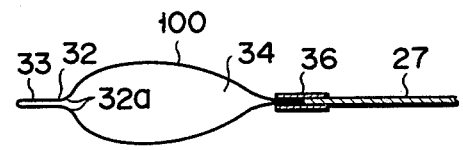
FIGS. 12 and 13 schematically show another embodiment of the latch.
Figure 13:
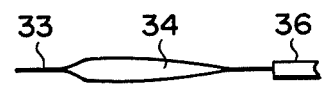

FIGS. 12 and 13 show another embodiment of a latch 28 also made of an elastic wire 100. Unlike in the above-described latches 28, a holding portion 33 of the wire 100 does not form a loop but is so U-shaped as to define the same gap as that of a neck 32 formed by the forward portions of the wire 100. The gap is narrower than the diameter of the film feeding wire 26, and thus the U-shaped holding portion 33 can hold the wire 26 steadfastly. Once clamped in the U-shaped portion 33, the wire 26 cannot slip out of the U-shaped portion 33, even if it is strongly pulled toward the distal end portion 13. This is because the stop 35 formed at the free end of the wire 26 cannot pass at all through the gap of the U-shaped loop portion 33.

Figure 14:
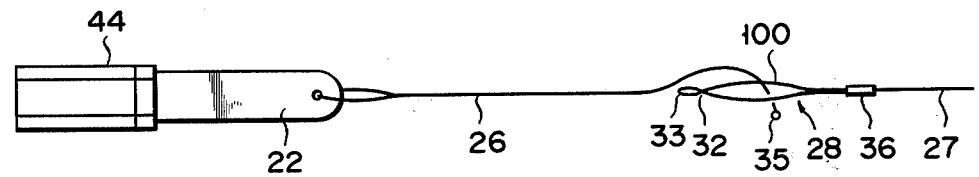
FIGS. 14 and 15 show arrangement of the latch used for another form of film cartridge.
Figure 15:
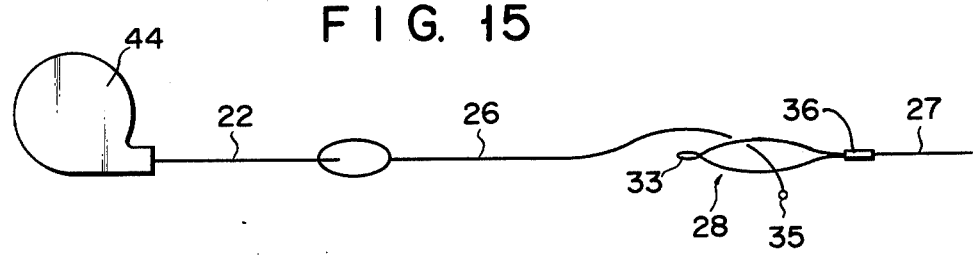

In the endoscope 11 shown in FIGS. 1 and 2, use is made of the film cassette 17 comprising the film containing section 18 and the film take-up section 19. Instead, another film cassette 44 as shown in FIGS. 14 and 15 may be used in the endoscope. In this case, a film feeding wire 26 is connected to the outer end of the film 22 in the cassette 44 and is pulled out at a time for a distance equal to a frame of the film 22.

In any of the above-described latches 28, the neck 32 (or portions 32a) and the smaller loop 33 (or U-shaped portion 33) constitute a latch section. The latch 28 according to this invention has a latch section which is simply constructed as mentioned above and which provides an easy connection and an easy disconnection between a film feeding wire and an operation wire. Further, it can be easily inserted into the thin guide pipe in an endoscope. It is therefore well fit for use in an endoscope, the distal end of which should be made as small and thin as possible.

To connect the film feeding wire to the operation wire, it is necessary merely to slip the film feeding wire into the smaller loop 33 (or U-shaped portion 33) through the neck 32. To disconnect the film feeding wire from the operation wire, it is sufficient to slip the film feeding wire out of the smaller loop 33 (or U-shaped loop portion 33) through the neck 32. In this way, both the connection and disconnection between said wires can be made easily and quickly, even in the semi-dark room and even by an endoscope operator affected by presbyopia.

What we claim is:

1. An endoscope comprising:
   a sheath;
   a distal end portion provided at one end of the sheath;
   a photographing device disposed in said distal end portion;
   a film feeding wire for feeding a rolled film loaded in said distal end portion;
   an operation wire extending through the sheath;
   a stop having a diameter larger than the diameter of the film feeding wire connected to one end of the film feeding wire; and
   a latch formed of an elastic wire for connection between respective ends of the film feeding wire and the operation wire and comprising
   a first loop connected to that one end of the operation wire which is disposed nearer said one end of the sheath,
   a second loop disposed opposite to said one end of the operation wire with respect to the first loop and having such an opening as prevents the stop from passing through, and a neck formed by those portions of the elastic wire which are between the first and second loops.

2. An endoscope according to claim 1, wherein said neck comprises said portions of said elastic wire which are arranged parallel with a smaller gap therebetween than the diameter of said film feeding wire.

3. An endoscope according to claim 1, wherein said neck comprises said portions of the elastic wire which are in contact with each other.

4. An endoscope according to claim 1, wherein said neck comprises said portions of said elastic wire which cross each other.

5. An endoscope according to claim 1, wherein said neck comprises said portions of said elastic wire which are twisted together.

* * * * *